(12) United States Patent
Simmons

(10) Patent No.: US 10,527,559 B2
(45) Date of Patent: *Jan. 7, 2020

(54) OPTICAL INSPECTION SYSTEM FOR PRINTED CIRCUIT BOARD OR THE LIKE

(71) Applicant: Robert Scott Simmons, West Chester, PA (US)

(72) Inventor: Robert Scott Simmons, West Chester, PA (US)

(*) Notice: Subject to any disclaimer, the term of this patent is extended or adjusted under 35 U.S.C. 154(b) by 34 days.

This patent is subject to a terminal disclaimer.

(21) Appl. No.: 15/926,836

(22) Filed: Mar. 20, 2018

(65) Prior Publication Data

US 2018/0209917 A1 Jul. 26, 2018

Related U.S. Application Data

(63) Continuation of application No. 14/548,385, filed on Nov. 20, 2014, now Pat. No. 9,952,162.

(60) Provisional application No. 61/915,583, filed on Dec. 13, 2013.

(51) Int. Cl.
*G01N 21/956* (2006.01)
*G01N 21/88* (2006.01)

(52) U.S. Cl.
CPC ....... *G01N 21/956* (2013.01); *G01N 21/8806* (2013.01); *G01N 2021/95638* (2013.01)

(58) Field of Classification Search
CPC ............. G01N 21/956; G01N 21/8806; G01N 2021/95638; G01N 21/88

USPC ........................................................... 348/87
See application file for complete search history.

(56) References Cited

U.S. PATENT DOCUMENTS

| | | | |
|---|---|---|---|
| 4,508,453 A * | 4/1985 | Hara | G01N 21/956 348/126 |
| 2003/0202092 A1* | 10/2003 | Sadighi | B25J 9/1692 348/87 |
| 2009/0225165 A1* | 9/2009 | Reneker | G01C 11/02 348/144 |
| 2010/0020167 A1 | 1/2010 | Zandifar | |
| 2012/0249739 A1 | 10/2012 | Gostynski | |
| 2013/0182100 A1* | 7/2013 | Aiko | G01N 21/9501 348/87 |
| 2013/0279655 A1* | 10/2013 | Ookawa | H05K 13/08 378/62 |

* cited by examiner

*Primary Examiner* — Thai Q Tran
*Assistant Examiner* — Nienru Yang
(74) *Attorney, Agent, or Firm* — Steven H. Meyer, Esq.

(57) ABSTRACT

An inspection system inspects points of interest on an item. A two-axis gimbal holds the item and is controlled to adjust an angle of incidence and angle of approach of a line of sight of an imaging device with respect to the point of interest. A Y-axis actuator adjusts a position of the imaging device along a Y-axis of the item, and an X-axis actuator adjusts a position of the imaging device along an X-axis of the item. A controller controls the gimbal, the Y-axis actuator and the X-axis actuator. Upon selecting a point of interest, angle of incidence, and angle of approach, the imaging device displays and/or captures an image, and the image can be inspected by a human inspector or automated inspection system.

11 Claims, 8 Drawing Sheets

OPTICAL INSPECTION SYSTEM FOR PRINTED CIRCUIT BOARD OR THE LIKE

CROSS-REFERENCE TO RELATED APPLICATION

The present application is a continuation of U.S. patent application Ser. No. 14/548,385, filed on Nov. 20, 2014, and entitled "OPTICAL INSPECTION SYSTEM FOR PRINTED CIRCUIT BOARD OR THE LIKE", hereby incorporated by reference in its entirety, which claims priority from U.S. Provisional Pat. Application No. 61/915,583, filed on Dec. 13, 2013, which is hereby incorporated by reference in its entirety.

FIELD

The present disclosure relates to an optical inspection system provided for printed circuit boards (PCBs) and printed circuit board assemblies (PCBAs). More particularly, the present disclosure relates to such an optical inspection system with increased control over the view of an optical image viewing and/or capturing device thereof. Specifically, in the present disclosure, the imaging device (hereinafter, 'camera') and a motor-controlled positioning system are provided to give an operator or a computer increased control over views available from the camera so as to be able to observe and/or record and analyze objects visible on a PCB or PCBA (hereinafter, 'board'). Even more specifically, in the present disclosure, the camera view can be controlled by specifying an X-Y and optionally Z coordinate (or the like) of a point on, above, or below the surface of the board, an angle of incidence to the surface of the board, an angle of approach to the surface of the board, and optionally a distance to the point.

BACKGROUND

As may be known, in manufacturing and/or otherwise producing printed circuit boards (PCBs) and printed circuit board assemblies (PCBAs) (i.e., 'boards', 'circuit boards', and the like), an important part of the manufacturing process is inspecting each board during and/or after manufacturing to ensure that the elements on each board are the correct parts and/or are properly placed, secured, and/or otherwise mounted to the board, and/or also to ensure that the board itself is proper. For example, it may be that each diode on the board should be inspected to ensure that the diode is not backward, and that a solder joint on the board that is particularly prone to error should be inspected to ensure such error has been avoided, among many other things.

In at least some instances, inspecting each board has been done manually by a human inspector who maneuvers to visually inspect the aspects of the board which require inspection, perhaps by picking up the board and moving same around to optimize such visual inspection while possibly using a visual aid such as a ring lamp, microscope, eyepiece, or other magnification device. As should be appreciated, though, picking up and moving the board for such visual inspection is to be discouraged for many reasons: touching the board improperly could impart a static shock that could damage the board; parts on the board may not necessarily be secured thereto when picked up and could be displaced from the board thereby; picking up the board disturbs the board from any previous alignment of the board that was achieved with regard to manufacturing machinery; picking up the board does not necessarily ensure an optimal view of a particular object on the board is achieved; and the like.

Picking up the board may be avoided, although performing a manual inspection of the board in such an instance may also be discouraged. For one thing, a human inspector may be hindered from visually inspecting the board in situ by the presence of the manufacturing machinery. For another thing, visually inspecting the board in situ may unreasonably require the human inspector to move about the board in an awkward manner in order to achieve a necessary view, or may unreasonably require the human inspector to assume an awkward position in order to achieve the necessary view. Moreover, regardless of whether the board is picked up, a human inspector may not be able to properly inspect an aspect of the board if, for example, lighting is inadequate, the aspect to be inspected is relatively small, the aspect is obstructed by another object on the board, and the like.

Accordingly, it is known that inspecting each board may be performed by or with the aid of an optical inspection system. Generally, with such an optical inspection system, one or more cameras or other imaging devices are maneuvered about the board in a controlled manner, and/or vice versa, so that aspects of the board to be inspected are captured and/or viewed as images. Each such image may then be compared to a reference image or numerically analyzed to determine whether the aspect is correct, either by a human inspector or by an automated computer process, or can be displayed on a monitor for viewing by the human inspector, for example.

Note, though, that prior optical inspection systems are either awkward or otherwise unsatisfactory. For example, some prior systems require multiple cameras, each of which is differently fixed with regard to the view obtained therefrom. Other prior systems also have cameras that are adjustable with regard to the view obtained therefrom, but in manners that are limited.

Accordingly, a need exists for an optical inspection system for printed circuit boards (PCBs) and printed circuit board assemblies (PCBAs) where the system includes a camera or other optical imaging device which is highly adjustable in an automated manner with regard to the view available therefrom. Specifically, a need exists for such a system with an imaging device whose view can be adjusted with regard to an X, Y position on a surface of a board under inspection, a Z height of the view on, above, or below the surface of the board, an angle of incidence with respect to the surface of the board, and an angle of approach with regard to the surface of the board. The view can then be displayed and/or captured so that a human operator or a computer algorithm can analyze images of the board as part of a manual, automatic, or semi-automatic inspection process.

SUMMARY

The aforementioned needs are satisfied by a system and method for inspecting points of interest on an item positioned with respect thereto, where the item has an X-Y plane associated therewith. In the system, an imaging device views and optionally captures an image of each point of interest. A two-axis gimbal holds the item and is controlled by one or more motors to adjust an angle of incidence of a line of sight of the imaging device with respect to the point of interest and an angle of approach of the line of sight of the imaging device with respect to the point of interest.

A Y-axis actuator holds the item and is controlled by a motor to adjust a position of the imaging device along a Y-axis of the item, and an X-axis actuator holds the item and is controlled by a motor to adjust a position of the imaging device along an X-axis of the item. A controller controls the motors of the gimbal, the Y-axis actuator and the X-axis actuator to control the line of sight of the imaging device with respect to the point of interest. The line of sight of the imaging device can be adjusted toward most any point of interest on the item at a selected angle of incidence and a selected angle of approach, an image of the point of interest can be viewed or captured, and thereafter the image can be inspected by at least one of a human inspector and an automated inspection system.

BRIEF DESCRIPTION OF THE DRAWINGS

The foregoing summary as well as the following detailed description of various embodiments of the present innovation will be better understood when read in conjunction with the appended drawings. For the purpose of illustrating the various embodiments of the innovation, there are shown in the drawings embodiments that are presently preferred. As should be understood, however, the innovation is not limited to the precise arrangements and instrumentalities shown. In the drawings.

DETAILED DESCRIPTION OF PREFERRED EMBODIMENTS

Figure 1:
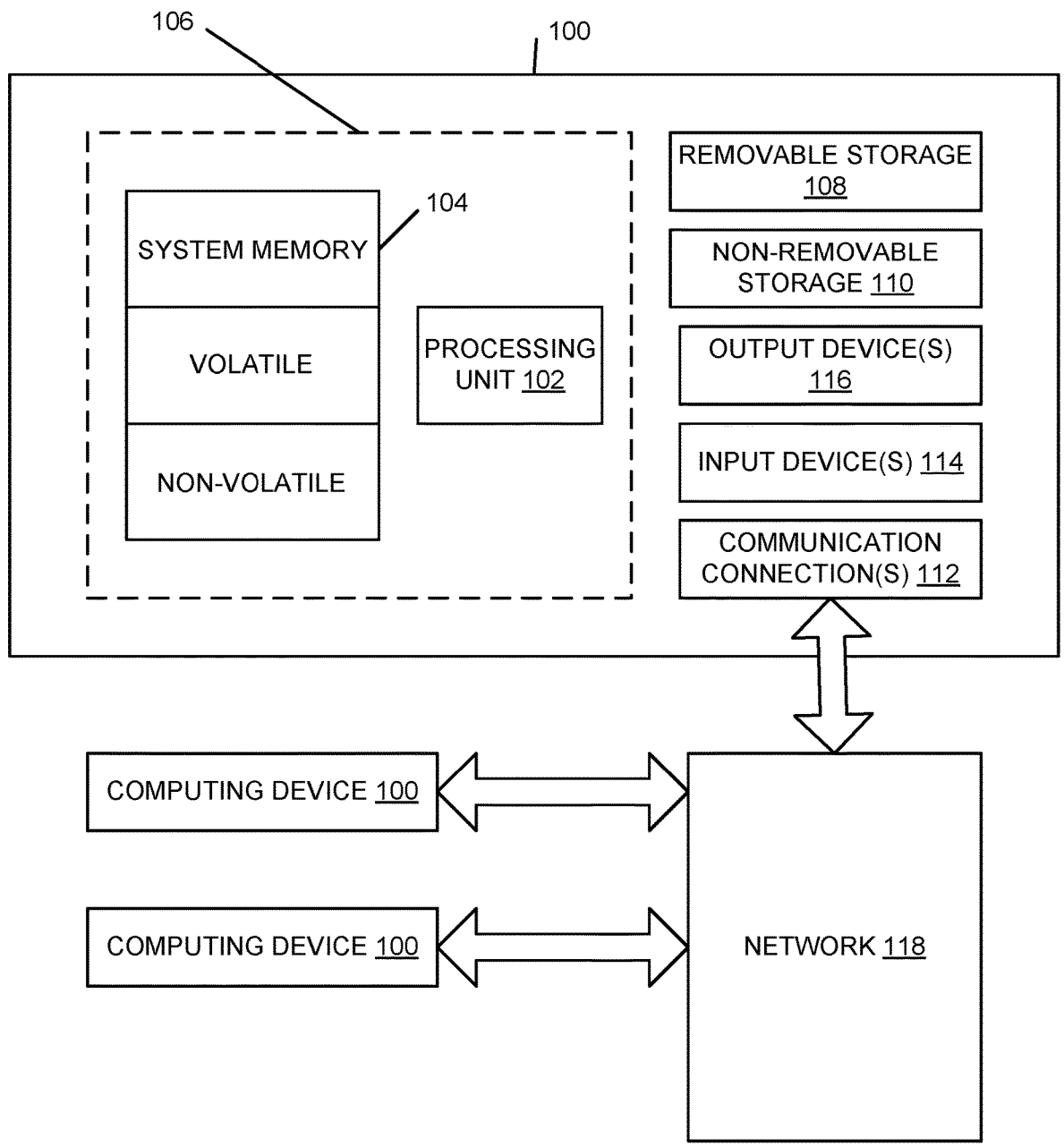
FIG. 1 is a block diagram of an example of a computing environment within which various embodiments of the present innovation may be implemented.

Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import.

Where a term is provided in the singular, the plural of that term is also contemplated unless circumstances clearly dictate otherwise. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by the relevant public. Although any methods and materials similar or equivalent to those described herein can be used in the practice or testing of the present innovation, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

Example Computing Environment

FIG. 1 is set forth herein as an exemplary computing environment in which various embodiments of the present innovation may be implemented. The computing system environment is only one example of a suitable computing environment and is not intended to suggest any limitation as to the scope of use or functionality. Numerous other general purpose or special purpose computing system environments or configurations may be used. Examples of well-known computing systems, environments, and/or configurations that may be suitable for use include, but are not limited to, personal computers (PCs), server computers, handheld or laptop devices including smart phones and computing tablets, multi-processor systems, microprocessor-based systems, network PCs, minicomputers, mainframe computers, embedded systems, distributed computing environments that include any of the above systems or devices, and the like.

Computer-executable instructions such as program modules executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 1, an exemplary system for implementing aspects described herein includes a computing device, such as computing device 100. In its most basic configuration, computing device 100 typically includes at least one processing unit 102 and memory 104. Depending on the exact configuration and type of computing device, memory 104 may be volatile (such as random access memory (RAM)), non-volatile (such as read-only memory (ROM), flash memory, etc.), or some combination of the two. This most basic configuration is illustrated in FIG. 1 by dashed line 106. Computing device 100 may have additional features and functionality. For example, computing device 100 may include additional storage (removable and/or non-removable) including, but not limited to, magnetic or optical disks or tape. Such additional storage is illustrated in FIG. 1 by removable storage 108 and non-removable storage 110.

Computing device 100 typically includes or is provided with a variety of computer-readable hardware media. Computer-readable media can be any available media that can be accessed by computing device 100 and includes both volatile and non-volatile media, removable and non-removable media. By way of example, and not limitation, computer-readable media may comprise computer storage media and communication media.

Computer storage media includes volatile and non-volatile, removable and non-removable media implemented in any method or technology for storage of information such as computer-readable instructions, data structures, program modules or other data. Memory 104, removable storage 108, and non-removable storage 110 are all examples of computer storage media. Computer storage media includes, but is not limited to, RAM, ROM, electrically erasable programmable read-only memory (EEPROM), flash memory or other memory technology, CD-ROM, digital versatile disks (DVD) or other optical storage, magnetic cassettes, magnetic tape, magnetic disk storage or other magnetic storage devices, or any other computer-readable hardware medium which can be used to store the desired information and which can be accessed by computing device 100. Any such computer storage media may be part of computing device 100.

Computing device 100 may also contain communications connection(s) 112 that allow the device to communicate with other devices 100. Each such communications connection 112 is an example of communication media. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection (including VoIP), and wireless media such as acoustic, radio frequency (RF), infrared, WiFi, and other wireless media. The term computer-readable media as used herein includes both storage media and communication media.

Computing device 100 may also have input device(s) 114 such as keyboard, mouse, pen, voice input device, touch input device, etc. Output device(s) 116 such as a display, speakers, printer, etc. may also be included. All these devices are generally known to the relevant public and therefore need not be discussed in any detail herein except as provided.

Notably, computing device 100 may be one of a plurality of computing devices 100 inter-connected by a network 118, as is shown in FIG. 1. As may be appreciated, the network 118 may be any appropriate network, each computing device 100 may be connected thereto by way of a connection 112 in any appropriate manner, and each computing device 100 may communicate with one or more of the other computing devices 100 in the network 118 in any appropriate manner. For example, the network 118 may be a wired or wireless network within an organization or home or the like, and may include a direct or indirect coupling to an external network such as the Internet or the like. Likewise, the network 118 may be such an external network.

Particularly in the case where the network 118 is an external network, such network 118 may be a digitally based network (including VoIP) for exchanging computer data among the devices 100, may be an audio and/or video network for exchanging audio and/or video data among the devices 100, or the like. Thus, it may be that the network 118 may be the Internet, a public switched telephone network for landline telephone communications, a mobile switching center for wireless telephone communications, a paging network for distributing paging information, a private multimedia network for establishing videoconferencing, or the like. Thus, it should be appreciated that one or more of the computing devices 100 that are shown to the left of the network 118 in FIG. 1 may be a mobile telephone, a landline telephone, a pager, a mobile electronic mail device, a desktop electronic mail device, a mobile electronic texting device, a desktop electronic texting device, or a combination thereof, or the like.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, so-called thumb drives and/or flash drives, or any other machine-readable storage medium wherein, when the program code is loaded into and executed by a machine, such as a computer, the machine becomes an apparatus for practicing the presently disclosed subject matter.

In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application-program interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language, and combined with hardware implementations.

Although exemplary embodiments may refer to utilizing aspects of the presently disclosed subject matter in the context of one or more stand-alone computer systems, the subject matter is not so limited, but rather may be implemented in connection with any computing environment, such as a network 118 or a distributed computing environment. Still further, aspects of the presently disclosed subject matter may be implemented in or across a plurality of processing chips or devices, and storage may similarly be effectuated across a plurality of devices in a network 118. Such devices might include personal computers, network servers, and handheld devices, for example.

Printed Circuit Boards/Board Assemblies

Figure 2:
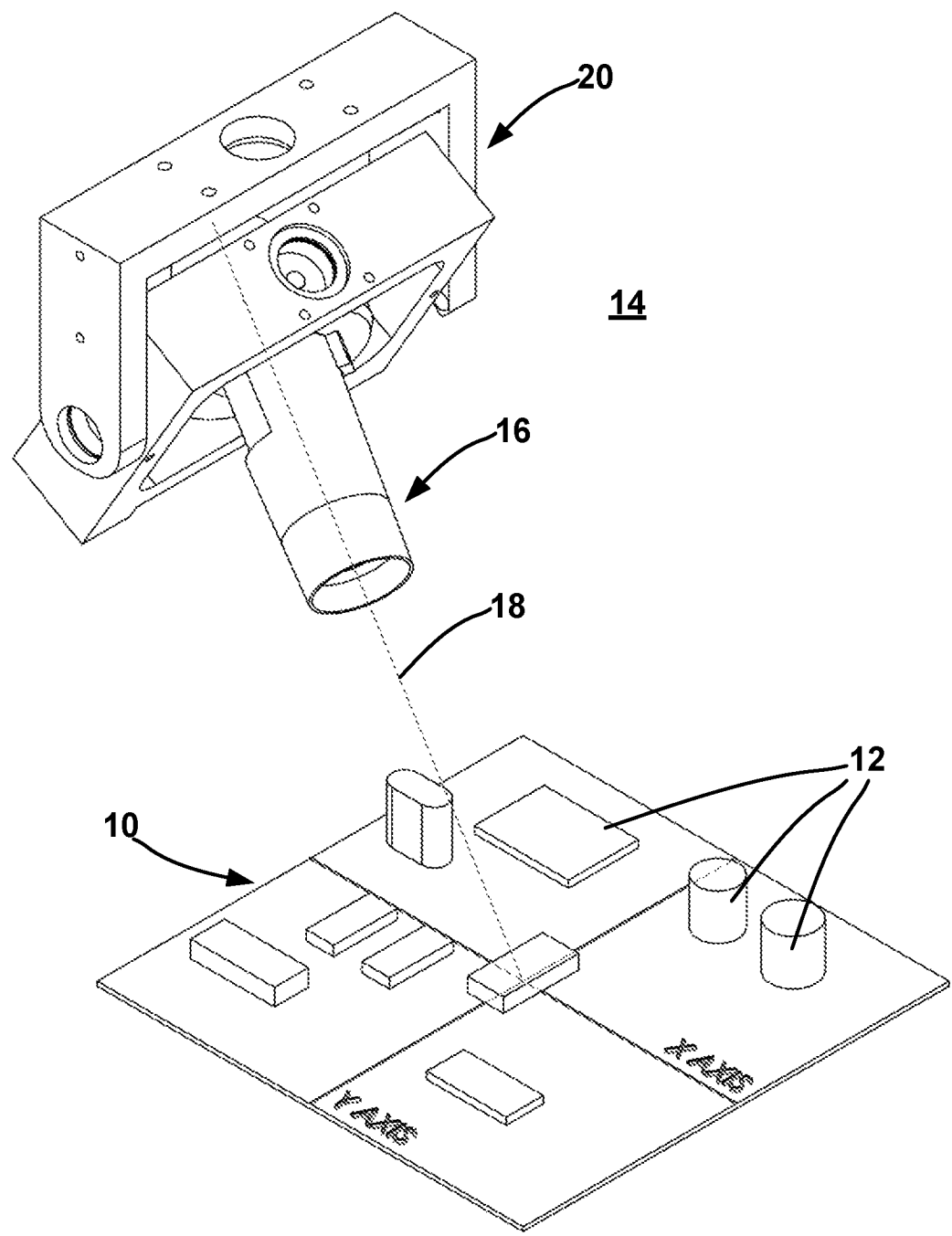
FIG. 2 is a conceptualized perspective view of the camera of an optical inspection system and a board mounted to the system in an embodiment of the present innovation.

Turning now to FIG. 2, a printed circuit board or circuit board assembly or the like (PCB/PCBA, hereinafter 'board') 10 is shown. The board 10 itself may have features or points of interest such as traces, pads, thru-holes, vias, coatings, or contaminants. Typically, although by no means necessarily, the board 10 has a plurality of objects 12 mounted thereto in some manner, either fixedly or to be fixed to the board 10. The board 10 and the objects 12 thereon may be most any board and objects without departing from the spirit and scope of the present innovation. For example, the objects 12 on the board 10 may include resistors, capacitors, inductors, electronic chips, electronic processors, mechanical connectors, electrical connectors, and the like.

Notably, each object 12 on the board 10 may be expected to be precisely placed with respect to the board 10, so as to align the object 12 with respect to particular features of the board 10 or with respect to another object 12 on the board.

Thus, and as an example, the connectors on an electronic chip may be required to be inserted within or placed on electrically connecting apertures or pads defined within the board 10, a diode may be required to be electrically mounted to a connector on the board 10 in a directionally specified manner, a wire may be required to electrically connect to a contact pad on the board 10, and/or the like.

Generally, the board 10 is itself mainly planar and thus each position on a surface of the board may be described according to an X-Y coordinate system. As a result, each object 12 on the board may also be described according to the X-Y coordinate system of the board 10, and in addition may have height features with respect to a height Z above or below the surface of the board 10. Such positions and describing according to an X-Y-Z coordinate system is generally known and therefore need not be set forth herein in any detail other than that which is provided.

Optical Inspection System

Figure 3:
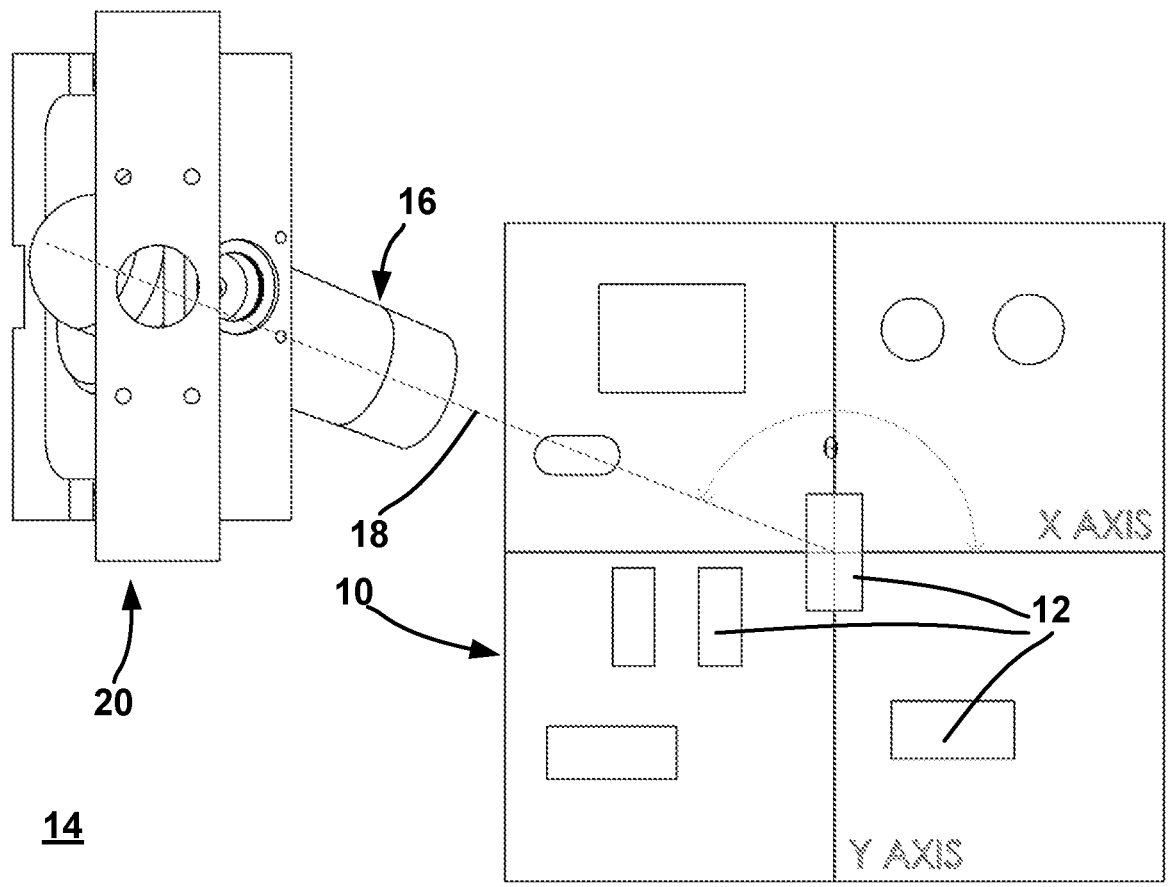
FIG. 3 is a conceptualized top view of the camera and board of FIG. 2 and shows the camera adjusted to a predetermined angle of approach with respect to the board in an embodiment of the present innovation.
Figure 4:
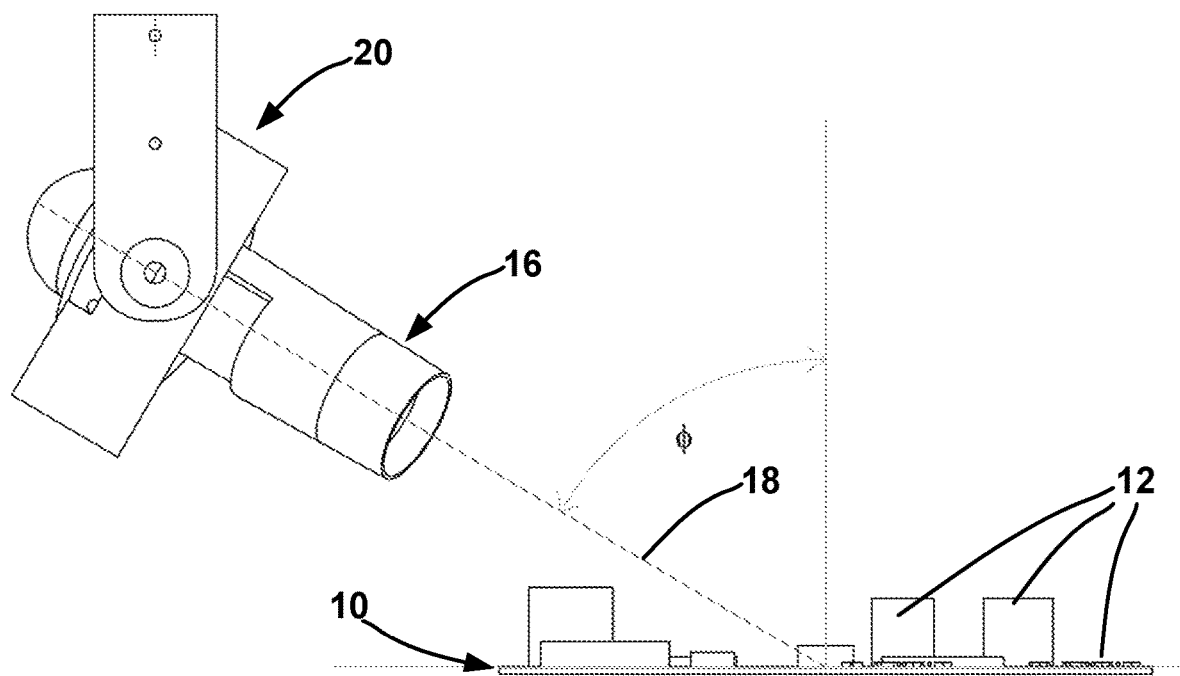
FIG. 4 is a conceptualized side view of the camera and board of FIG. 2 and shows the camera adjusted to a predetermined angle of incidence with respect to the board in an embodiment of the present innovation.

As was alluded to above, in manufacturing and/or otherwise producing the board 10, an important part of the manufacturing process is inspecting the board during and/or after manufacturing to ensure that the objects 12 on the board 10 are the correct part and/or are properly placed, secured, and/or otherwise mounted to the board 10, and/or to ensure that the board 10 itself is proper. Accordingly, and referring to FIGS. 2-4, it is seen that the board 10 has been mounted or otherwise positioned and aligned in a predetermined manner with respect to an optical inspection system 14 of the present disclosure. Note here that while X-Y axes have been defined in a particular manner for the board 10 as shown in FIGS. 2-4, such X-Y axes can be defined in other manners, and such X-Y axes of the board 10 are not necessarily aligned with X-Y axes defined for the system 14 or objects 12. Mounting and aligning the board 10 is generally known or should be apparent to the relevant public and therefore need not be set forth herein in any detail other than that which is provided.

Notably, and as best shown in FIG. 2, the system 14 includes a camera 16 or the like for viewing and/or capturing images from the mounted board 10. Presumptively, although not necessarily, the camera 16 is a digital camera for viewing and/or capturing digital images. Alternately, the camera 16 may be purely optical in nature or based on an alternate format without departing from the spirit and scope of the present innovation. Such a camera 16 is known or should be apparent to the relevant public, and therefore may be most any appropriate camera 16 without departing from the spirit and scope of the present innovation. Notably, the camera points along a predetermined line 18 of sight, and in various embodiments of the present innovation the camera 16 and the line 18 of sight is highly adjustable, in a manner that will be set forth in more detail below.

Specifically, in various embodiments of the present innovation, the camera 16 is held by a gimbal 20 or the like. As best seen in FIG. 2, the gimbal 20 is a two-axis angle-adjustable gimbal, although other gimbals may be employed without departing from the spirit and scope of the present innovation. The two-axis gimbal 20 may be controlled by one or more motors 22 (FIGS. 5 and 6) of appropriate type, such as for example stepper motors or servo motors. Such motors 22 are known or should be apparent to the relevant public, and therefore may be most any appropriate motors without departing from the spirit and scope of the present innovation.

Notably, with the camera 16 mounted to the gimbal 20, the line 18 of sight of the camera may be finely adjusted to most any angle of approach and angle of incidence with respect to the board 10. In particular, and with reference to FIG. 3, the motors 22 of the gimbal 20 may be adjusted so as to point the line 18 of sight of the camera 16 along a predetermined angle of approach ($\theta$ in FIG. 3), where such angle of approach may be defined as the angle of the line 18 projected to the plane (i.e., the X-Y plane) of the board 10 with respect to a predetermined reference, which in the case of FIG. 3 is the positive portion of a line parallel to an X-axis in the plane of the board 10. As shown in FIG. 3, the angle of approach is about 155 degrees (counter clockwise) from a three o'clock position, but may alternately be described with regard to a different reference, such as for example 65 degrees from a twelve o'clock position.

Similarly, and with reference to FIG. 4, the motors 22 of the gimbal 20 may be adjusted so as to point the line 18 of sight of the camera 16 along a predetermined angle of incidence ($\phi$ in FIG. 4), where such angle of incidence may be defined as the angle of the line 18 with respect to a line normal to the plane of the board 10, which in the case of FIG. 3 is the positive portion of a line parallel to the Z-axis with respect to the X-Y plane of the board 10. As shown in FIG. 4, the angle of incidence is about 60 degrees from normal, but may alternately be described as being 30 degrees with respect to the X-Y plane of the board 10.

Figure 5:
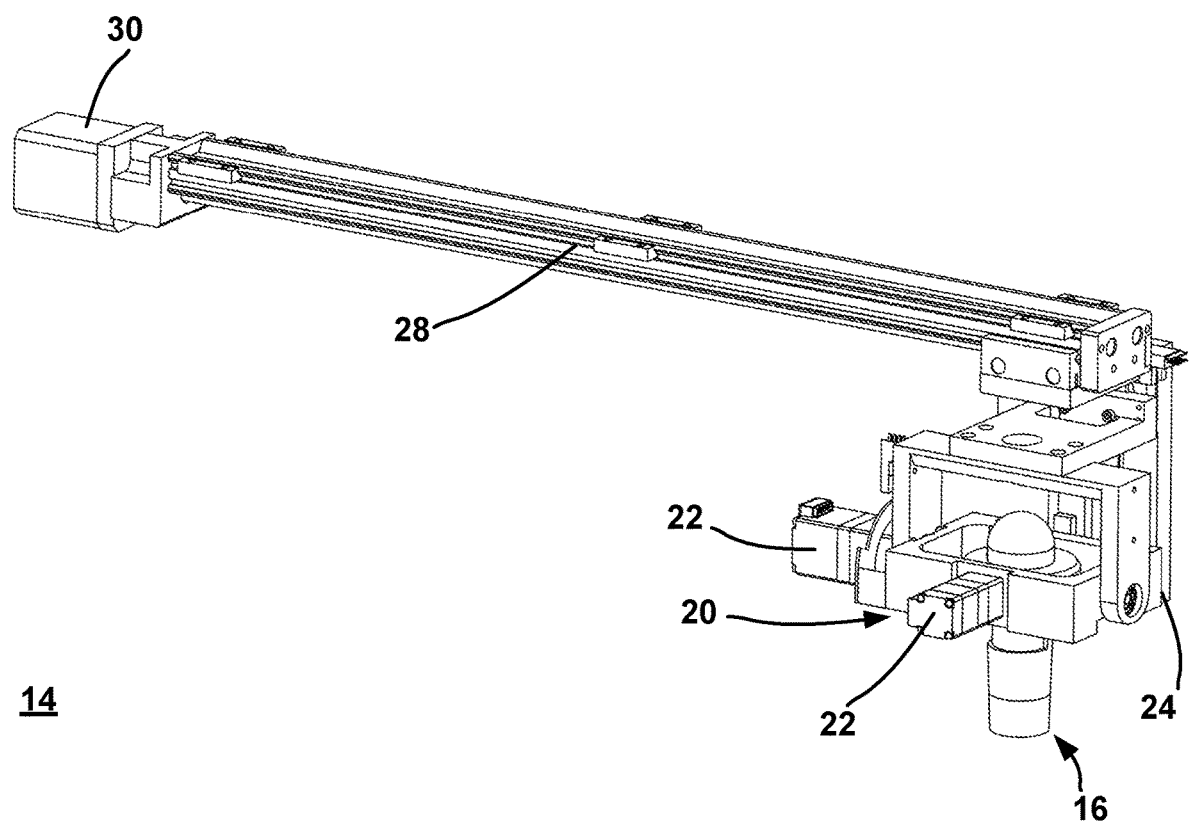
FIG. 5 is a conceptualized perspective view of the camera of FIG. 2 as well as additional elements of the optical inspection system in an embodiment of the present innovation.
Figure 6:
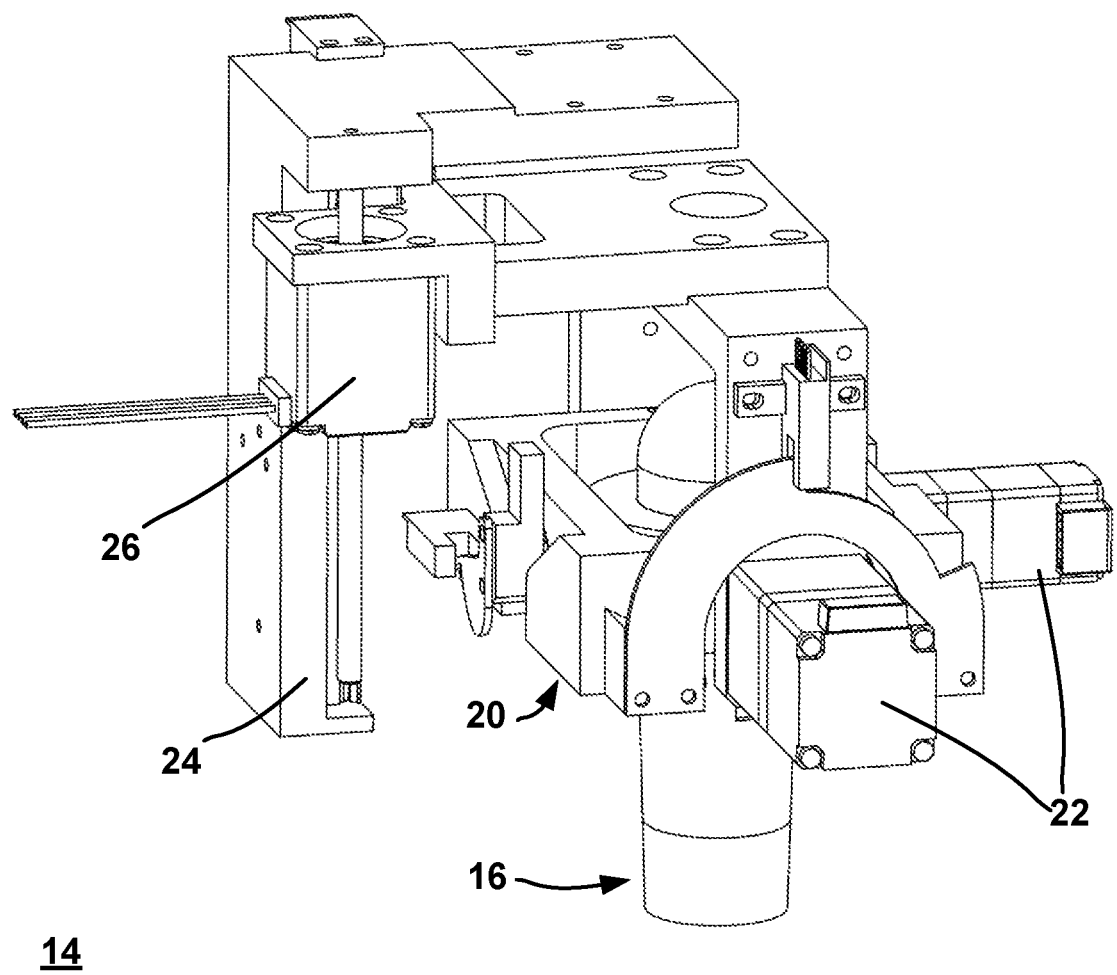
FIG. 6 is a more detailed perspective view of the camera and adjacent elements of FIG. 5 in an embodiment of the present innovation, taken generally from the left side of FIG. 5 looking toward the right.

As should now be apparent, with the gimbal 20, the angle of incidence and angle of approach of the line 18 of sight of the camera 16 may be adjusted with respect to a board 10 mounted to the system 14. Turning now to FIGS. 5 and 6, it is seen that the height of the camera 16 above the X-Y plane of the board 10 also may be adjusted, here by way of a Z-axis slide 24 (FIGS. 5 and 6) to which the gimbal 20 is mounted and a Z-axis motor 26 (FIG. 6) of appropriate type, such as for example a stepper or servo motor. As with motors 22, motor 26 is known or should be apparent to the relevant public, and therefore may be most any appropriate motor without departing from the spirit and scope of the present innovation. Likewise, the Z-axis slide 24 is known or should be apparent to the relevant public, and therefore may be most any appropriate slide without departing from the spirit and scope of the present innovation.

As also seen in FIG. 5, the Y position of the camera 16 above the X-Y plane of the board 10 may be adjusted, here by way of a Y-axis actuator 28 to which the Z-axis slide 24 is mounted and a Y-axis motor 30 of appropriate type, such as for example a stepper or servo motor. Similarly, and referring now to FIG. 7, the X position of the camera 16 above the X-Y plane of the board 10 may be adjusted, here by way of an X-axis actuator 32 to which the Y-axis actuator 28 is mounted in a generally perpendicular manner and an X-axis motor 34 of appropriate type, such as for example a servo motor. As with motors 22 and 26, motors 30 and 34 are known or should be apparent to the relevant public, and therefore may be most any appropriate motors without departing from the spirit and scope of the present innovation. Likewise, the Y-axis actuator 28 and the X-axis actuator 32 are known or should be apparent to the relevant public, and therefore may be most any appropriate actuator without departing from the spirit and scope of the present innovation.

Figure 7:
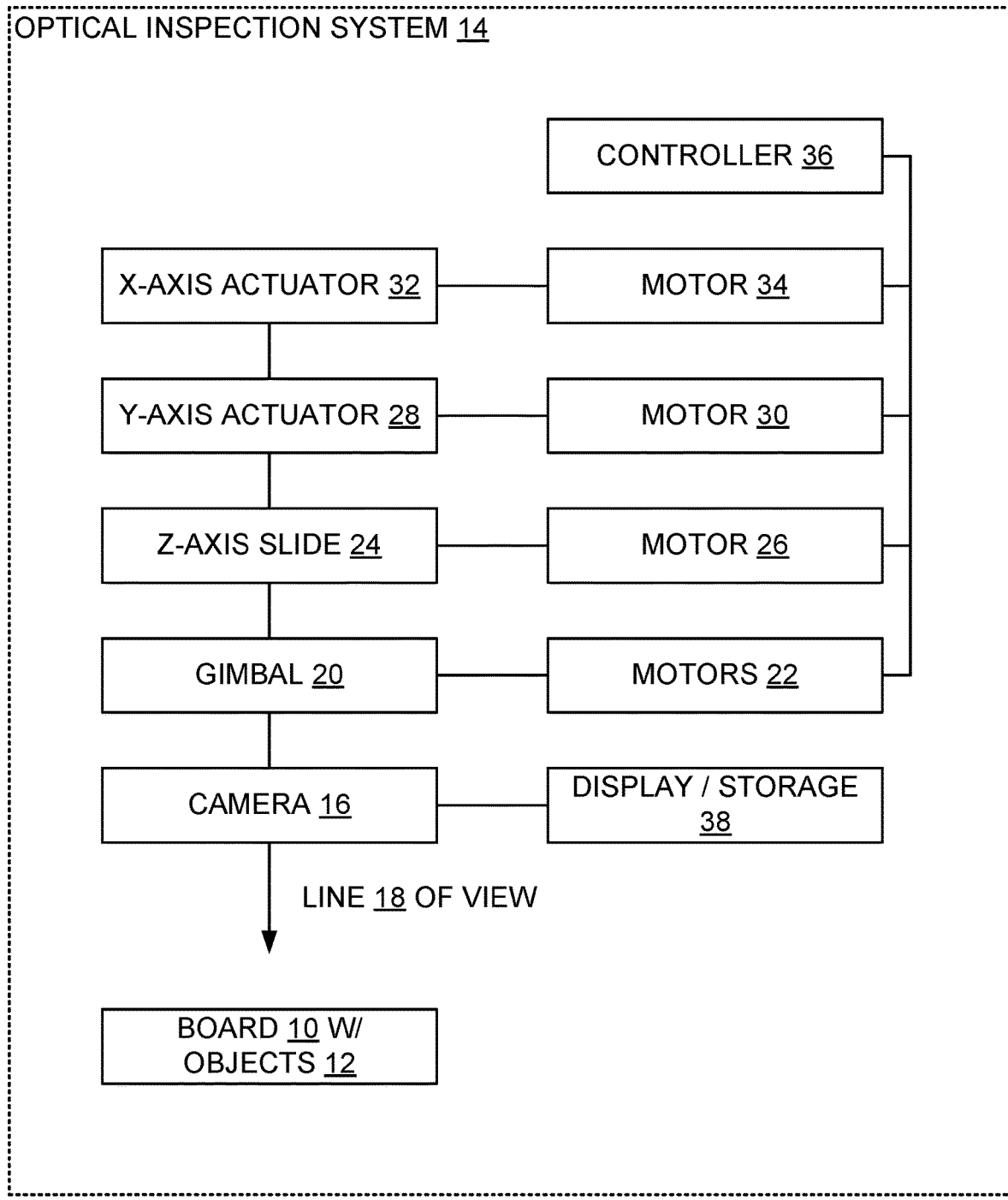
FIG. 7 is a block diagram of FIG. 2 et seq. including additional details in an embodiment of the present innovation.

Turning now to FIG. 7, it is seen that the elements of the system 14 are more conceptually represented. Notably, it is to be understood that although one element may be shown in FIG. 7 or another drawing as being mounted to another element, such elements may alternately be re-arranged if deemed necessary or advisable without departing from the spirit and scope of the present innovation. For example, although the Y-axis actuator 28 is shown as being mounted to the X-axis actuator 32, the X-axis actuator 32 may alternately be mounted to the Y-axis actuator 28. Notably, in the system 14 of the present innovation, the combination of the actuator 28, 32, the slide 24, the gimbal 20, and the related motors 22, 26, 30, 34 allows the camera 16 to be finely adjusted so as to view most any X-Y point on the plane of the board 10, and any height Z above or below that point on the surface of the board by way of a line 18 of sight having a selected angle of incidence and a selected angle of approach.

As may be apparent, the functionality of the gimbal 20, Z-axis slide 24, the Y-axis actuator 28, and the X-axis actuator 32 may be rearranged into other structures without departing from the spirit and scope of the present innovation. For example, it may be that the Y-axis actuator 28 and the X-axis actuator 32 are alternately incumbent in an overhead gantry or the like, or that the Z-axis slide 24 is present in the structure of the gantry itself, or that the structures are rearranged upside down to look up at the bottom surface or underside of the board 10, or that the board 10 itself is moved by some combination of the X- and Y-axis actuators 32, 28, and/or Z-axis slide 24 to position the point of interest with respect to the camera 16.

Note that, as seen in FIG. 7, in the system 14, the motors 22, 26, 30, 34 are controlled by a controller 36 in an appropriate manner so as to control the line 18 of sight of the camera 16 with respect to the board 10. Accordingly, and again, camera 16 can be finely adjusted so as to view most any X-Y point on the plane of the board 10, or at any height Z above or below that point on the surface of the board by way of a line 18 of sight having a selected angle of incidence and a selected angle of approach. Thus, in the system 14, an image can be viewed or captured from the board 10 and thereafter such image can be delivered to a display and/or storage device 38 to be inspected by a human inspector and/or an automated computer inspection system (not shown). As should be appreciated, operation of the controller 36 and display/storage 38 is known or should be apparent to the relevant public and therefore need not be set forth in detail herein other than that which has been provided. Accordingly, the controller 36 and display/storage 38 may be any appropriate controller and display/storage without departing from the spirit and scope of the present innovation.

The present innovation resides among other things in the ability to control both the viewing angle of incidence and angle of approach to the surface of the board 10, while viewing the item or object 12 or portion thereof located at a height Z above or below an X-Y point on the surface of the board 10. As should be appreciated, the ability to control the angle of incidence and the angle of approach is highly useful when inspecting the board 10 for a number of reasons including, but not limited to the following:

For through-hole parts, the identifying numbers of the parts may be located on the sides of the parts where the view may be obstructed by other parts. This may make it necessary to view the part at unusual angles of incidence and approach.

For some parts, a solder joint to be inspected is slightly under the part. This may make it necessary to view the part at unusual angles of incidence and approach.

For some parts, the solder joint to be inspected can be under the part, with the view obstructed by the legs of the part or other obstructions. This makes it necessary to view the joint at unusual angles of incidence and approach.

In the present innovation, the camera 16 is moved with respect to the board 10 while the board 10 is maintained as stationary. In various embodiments, the board 10 is instead or in addition moved, although it is appreciated that maintaining the board 10 as stationary and moving only the camera 16 is more suitable in at least some instances. As should be appreciated, keeping the board 10 stationary allows objects 12 thereon to be loosely mounted by for example not being soldered in place. However, with a moving board 10, loose parts can shift out of place.

Notably, gimbal 20 allows for any angle of approach without limit (i.e., from 0 to 360 degrees) or return requirement once a limit is met. In contrast, other configurations may have a limited range for angle of approach and require a stop and return once a rotation limit is encountered. Also, using a gimbal 20 to hold the camera 16 by its nature fixes the view of the camera 16 to have a normalized orientation, whereby 'up' in an image displayed or captured by the camera 16 is always in the same direction with respect to the X-Y plane of the board 10. Thus, the gimbal 20 allows the camera 16 to be maintained in the same orientation of alignment with X and Y. This is an advantage when reviewing images displayed or captured from the board 10, because the orientation of the images matches the orientation of the PCB. In contrast, other configurations may rotate the camera 16 or board 10 so that the X-Y alignment of the captured image to 'up' would be lost, which to at least a human inspector is highly disorienting.

The system 14 is operated in the following manner. For a top-down view, gimbal 20 would be adjusted so that the line 18 of sight of the camera 16 has an angle of incidence of 0, which is to say that the line 18 of sight would be normal to the X-Y surface of the board 10. Note here when the angle of incidence is 0, the angle of approach is essentially irrelevant, or null. All that need be supplied, then, is a set of X-Y or X-Y-Z coordinates with respect to the board 10 corresponding to a particular point of interest on the board 10 or of a point on an object 12 of interest. Thus, a view of the point of interest on item 10 or of a point of interest on object 12 can be displayed or captured for storage and or viewing to inspect same.

Figure 8:
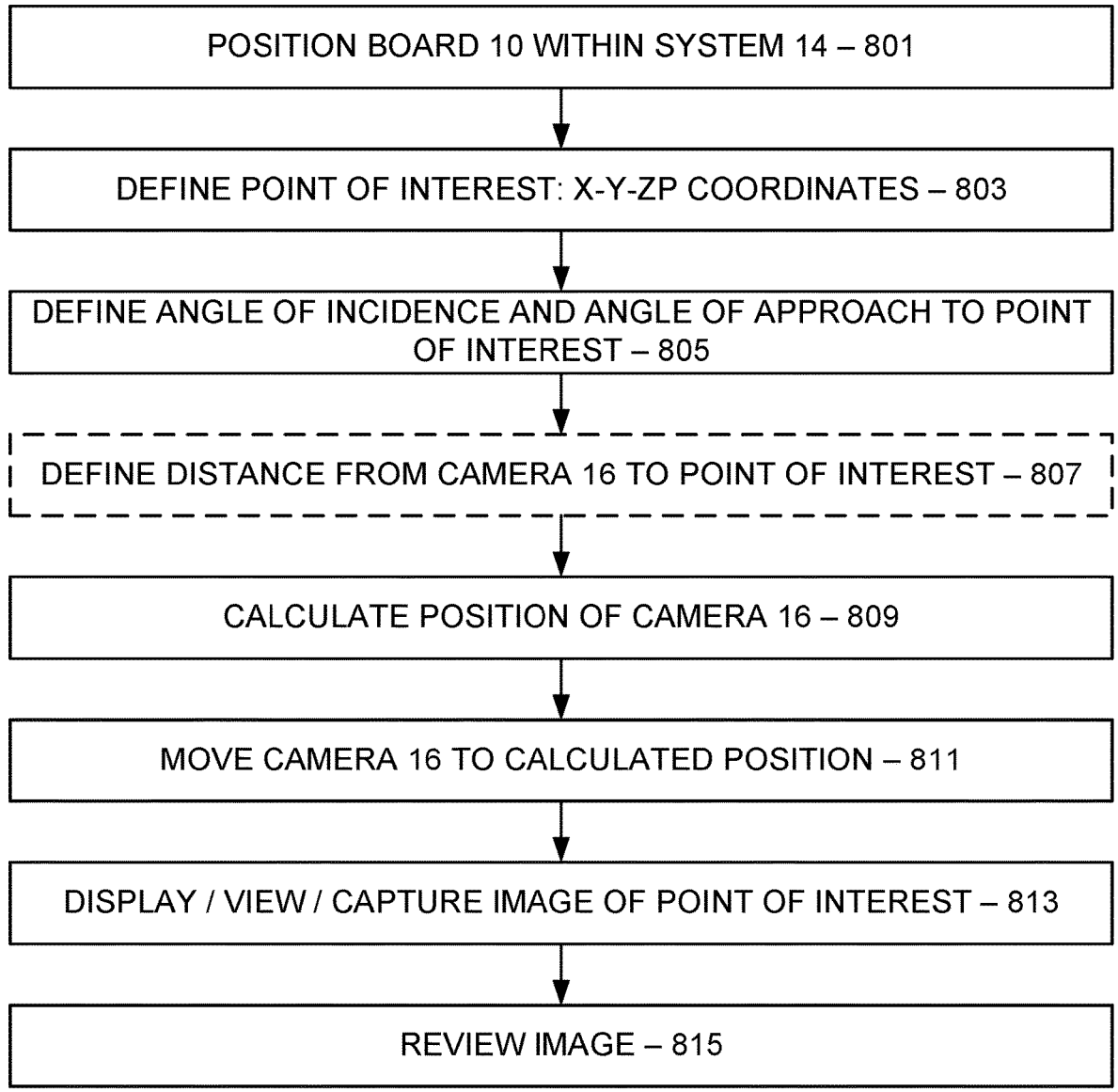
FIG. 8 is a flow diagram showing actions taken in connection with the system of FIG. 2 et seq.

Turning now to FIG. 8, an angled view of a point on the board 10 or on an object 12 of interest on the board is more involved. Preliminarily, the particular point on the board 10 or of the object 12 of interest (i.e., 'point of interest') is defined in terms of a set of X-Y coordinates on the board 10, and in terms of a height Z above or below the surface of the board 10 (803). Thereafter, the angle of incidence and angle of approach to the particular point of interest are defined (805), as may be the distance of the camera 16 from the point of interest (807). Thereafter, calculations are performed by the controller 36 to define how to position the camera 16, where such calculations result in a position that the motor 34 is to move the X-axis actuator 32, a position that the motor 30 is to move the Y-axis actuator 28, a position that the motor 26 is to move the Z-axis slide 24, and a position that the motors 22 are to position the gimbal 20 holding the camera 16 (809).

Note here that in at least some instance the distance of the camera 16 from the point of interest need not necessarily be adjustable or be required to be held constant, while still being within the spirit and scope of the present innovation. For example, if the depth of field of the camera 16 is relatively large, or camera 16 has auto-focus or can be focused by computer control, it may be the case that the camera 16 can focus clearly on a point of interest from a relatively large range of distances, in which case the distance of the camera 16 from the point of interest is not especially significant and can be highly variable and need not be controlled or required to be held constant. In contrast, if the depth of field of the camera 16 is relatively small, it may be the case that the camera 16 can focus clearly on a point of interest from a relatively small range of distances and may not have auto-focus or the like, in which case the distance of the camera 16 from the point of interest is more significant and perhaps limited to a relatively small range.

As should be understood, the calculations of 809 are expected to be performed by software or the like executed by or on behalf of the controller 36, presumptively in a manner transparent to a human inspector or other user. Generally, the calculations are expected to be trigonometric in nature, to determine how to align the camera 16 so as to set the line 18 of sight to the point of interest, while perhaps maintaining the distance of the camera 16 from the point of interest as set at 807. The specific calculations and other algorithms incumbent in the software are known or should be apparent to the relevant public and therefore need not be set forth herein in any detail other than that which is provided. Accordingly, such software may be any appropriate software without departing from the spirit and scope of the present innovation.

At any rate, the camera 16 is properly positioned within the system 14 and with regard to the board 10 mounted thereto based on the calculation of 809 (811), one or more images of the point of interest may be viewed and/or captured for transfer to the display and/or storage device 38 (813), and then reviewed (815). Of course, prior to image display or capture, the board 10 must be properly positioned within and otherwise mounted to the system 14 so that the point of interest is indeed at the X-Y-Z position at which such point of interest is expected to be found (801). Correctly mounting or positioning the board 10 in a location expected by the system 14 is known or should be apparent to the relevant public and therefore need not be set forth herein in any detail other than that which is provided. Accordingly, such mounting or positioning may be performed in any appropriate manner and with any appropriate mechanism without departing from the spirit and scope of the present innovation.

Typically, although not necessarily, the system 14 can be expected to be employed to inspect multiple points of interest on the board 10, perhaps in an automated manner. Accordingly, it may be that the controller 36 of the system 14 includes or has access to a list of each such point of interest, including the X-Y-Z coordinate thereof or at least information from which such coordinate may be derived, the desired angle of incidence and angle of approach to the point of interest, and optionally any desired distance of the camera 16 from the point of interest, as at 803-807. Thus, the controller may employ such information to move the camera 16 about the board 10 as at 811 and display or capture the desired images as at 813 for review as at 815.

In at least some instances, the aforementioned information is provided from multiple lists. For example, it may be that a first list includes for the board 10 a list of objects 12 thereon and for a center point or other reference point of each object 12 an X-Y or X-Y-Z position and rotation of the center point or reference point of object 12 from a standard position. Note here that the X-Y-Z positions of center points or reference points of the objects 12 on the board may be relative to some origin on the board 10 and not necessarily to an origin of the system 14, in which case appropriate translation may be required.

With such a first list, reference may then be made to a second list of points of interest to be inspected on at least some of the objects 12 from the first list, including for each listed point of interest an X-Y-Z offset from the center point or reference point of the corresponding object 12 from the first list, and a desired angle of incidence and angle of approach for the desired view corresponding to the point of interest. Thus, for each object 12 in the first list, multiple views of or relating to the object 12 can be obtained by use of the information in the second list. The calculations of 809, movement of 811, display or capture of 813, and review of 815 may then be performed for each point of interest.

In the embodiments thus far set forth, the camera 16 is moved with respect to the board 10 while the board 10 is maintained as stationary. As was noted above, though, the board 10 can instead or in addition be moved. As may be appreciated, such board movement is useful in at least some circumstance, such as for example where the camera 16 is restricted in movement or is held stationary, where a view of the camera 16 (or of an inspector) must be fixed due to external considerations, or the like. In such circumstances, and in various embodiments of the present innovation, the board 10 may be made to be movable by being held by moving structures, perhaps in a manner similar to the way the camera 16 has heretofore been disclosed as being movably held.

For example, and as should now be understood, it may be that the board 10 is held by X-axis and Y-axis actuators such as X-axis and Y-axis actuators 32, 28, which in turn may be held by a gimbal such as gimbal 20, which in turn may be held by a Z-axis slide such as Z-axis slide 24, although other arrangements are also envisioned. Thus, moving such holding elements would move the board 10 and the X-Y plane thereof with respect to camera 16. As before, with the board 10 movable, the line 18 of sight of the camera 16 may be finely adjusted to most any angle of approach and angle of incidence with respect to the board 10. Likewise, the board 10 may be maneuvered so as to move most any point of interest on the board into the line 18 of sight of the camera 16.

Conclusion

The programming believed necessary to effectuate the processes performed by the controller 26 and system 14 in connection with the various embodiments of the present innovation is relatively straight-forward and should be apparent to the relevant programming public. Accordingly, such programming is not attached hereto. Any particular programming, then, may be employed to effectuate the various embodiments of the present innovation without departing from the spirit and scope thereof.

In the present innovation, an optical inspection system 14 is provided for inspecting boards 10 such as printed circuit boards (PCBs) and printed circuit board assemblies (PCBAs), where the system 14 includes a camera 16 or other optical and/or digital imaging device which is highly adjustable in an automated manner with regard to the view available therefrom. Specifically, the line 18 of sight of the camera 16 can be adjusted with regard to an X-Y and/or X-Y-Z position of a point of interest on the board 10 under inspection, an angle of incidence with respect to the surface of the board 10, and an angle of approach with regard to the surface of the board 10. A human inspector or a computer algorithm can then view, and/or capture, and/or analyze images of the board 10 as part of a manual, automatic, or semi-automatic inspection process.

It should be appreciated that changes could be made to the embodiments described above without departing from the innovative concepts thereof. For example, although the present innovation is set forth primarily in terms of a board 10 of an electrical nature, other boards 10 and items may likewise be inspected with the system 14 with appropriate modification, such as for example manufactured mechanical parts, mechanical assemblies, or electromechanical assemblies. Likewise, although the present innovation may be set forth with reference to an X-Y-Z coordinate system, the innovation may also be employed with reference to other coordinate systems with appropriate modification. It also follows that the system 14 is not limited to controlling the line 18 of site of an optical device. The system 14 could for example control the view or line 18 of site of an X-ray, infrared, or other type of device that a controlled line of site and or distance from a point is required. It should be understood, therefore, that this innovation is not limited to the particular embodiments disclosed, but it is intended to cover modifications within the spirit and scope of the present innovation as defined by the appended claims.

The invention claimed is:

1. An inspection system for inspecting points of interest on an item positioned with respect thereto, the item being a circuit board or circuit board assembly ("circuit board") having a plurality of objects mounted thereto and having an X-Y plane associated therewith, the system comprising:
    an imager for viewing and/or capturing an image of each point of interest on the circuit board, the imager having a line of sight;
    a two-axis gimbal holding the circuit board, the gimbal being controlled by one or more motors to adjust an angle of incidence of the line of sight of the imager with respect to the point of interest and an angle of approach of the line of sight of the imager with respect to the point of interest, the angle of incidence being an angle of the line of sight with respect to a line normal to the X-Y plane of the circuit board, the angle of approach being an angle of the line of sight projected to the X-Y plane of the circuit board with respect to a predetermined reference;
    a Y-axis actuator holding the circuit board, the Y-axis actuator being controlled by a motor to adjust a position of the imager along a Y-axis of the circuit board;
    an X-axis actuator holding the circuit board, the X-axis actuator being controlled by a motor to adjust a position of the imager along an X-axis of the circuit board, the Y-axis actuator and the X-axis actuator being incumbent in a gantry;
    a Z-axis slide holding the circuit board, the Z-axis slide being controlled by a motor to adjust a height of the imager above the X-Y plane of the circuit board; and
    a controller controlling the motors of the gimbal, the Z-axis slide and the Y-axis actuator and the X-axis actuator of the gantry to control the line of sight of the imager with respect to the point of interest, the controller receiving inputs including:
    a set of coordinates with respect to the circuit board and corresponding to the point of interest,
    a predetermined angle of incidence to the point of interest which the line of sight of the imager is to be set, and
    a predetermined angle of approach to the point of interest which the line of sight of the imager is to be set,
    the controller calculating a position to move the circuit board by way of the Z-axis slide and the Y-axis actuator and the X-axis actuator of the gantry to set the line of sight toward the point of interest when the imager is at the inputted predetermined angle of incidence and the inputted predetermined angle of approach, the calculated position being calculated from the inputted set of coordinates, the inputted predetermined angle of incidence and the inputted predetermined angle of approach,
    the controller moving the motors of the gimbal to set the circuit board to the inputted predetermined angle of incidence and the inputted predetermined angle of approach, and
    the controller moving the motors of the Z-axis slide and the Y-axis actuator and the X-axis actuator of the gantry to set the circuit board to the calculated position, wherein an image of the point of interest can be viewed and/or captured from the set circuit board at the calculated position and at the predetermined angle of incidence and the predetermined angle of approach, and thereafter the image can be inspected by at least one of a human inspector and an automated inspection system.

2. The system of claim 1 wherein the controller moves the item with respect to the imager while the imager is maintained as stationary.

3. The system of claim 1 wherein the gimbal holding the item fixes the view of the imager to have a normalized orientation so that an 'up' direction in an image captured by the imager is always in a fixed direction with respect to the X-Y plane of the item.

4. The system of claim 1 wherein the item is mounted to a first one of the Y-axis actuator and the X-axis actuator, the first one of the Y-axis actuator and the X-axis actuator is mounted to the second one of the Y-axis actuator and the X-axis actuator, and the second one of the Y-axis actuator and the X-axis actuator is mounted to the gimbal.

5. A method of operating an inspection system for inspecting points of interest on an item positioned with respect thereto, the item being a circuit board or circuit board assembly ("circuit board") having a plurality of objects mounted thereto and having an X-Y plane associated therewith, the system comprising:
    an imager for viewing and/or capturing an image of each point of interest on the circuit board, the imager having a line of sight;
    a two-axis gimbal holding the circuit board, the gimbal being controlled by one or more motors to adjust an angle of incidence of the line of sight of the imager with respect to the point of interest and an angle of approach of the line of sight of the imager with respect to the point of interest, the angle of incidence being an angle of the line of sight with respect to a line normal to the X-Y plane of the circuit board, the angle of approach being an angle of the line of sight projected to the X-Y plane of the circuit board with respect to a predetermined reference;
    a Y-axis actuator holding the circuit board, the Y-axis actuator being controlled by a motor to adjust a position of the imager along a Y-axis of the circuit board;
    an X-axis actuator holding the circuit board, the X-axis actuator being controlled by a motor to adjust a position of the imager along an X-axis of the circuit board, the Y-axis actuator and the X-axis actuator being incumbent in a gantry; and
    a controller controlling the motors of the gimbal, the Z-axis slide, the Y-axis actuator, and the X-axis actuator to control the line of sight of the imager with respect to the point of interest,
    the method comprising the controller:
    receiving as an input a set of coordinates with respect to the circuit board and corresponding to the point of interest;
    receiving as an input a predetermined angle of incidence to the point of interest which the line of sight of the imager is to be set;

receiving as an input a predetermined angle of approach to the point of interest which the line of sight of the imager is to be set;

calculating a position to move the circuit board to by way of the Z-axis slide and Y-axis actuator and the X-axis actuator of the gantry to set the line of sight toward the point of interest when the imager is at the inputted predetermined angle of incidence and the inputted predetermined angle of approach, the calculated position being calculated from the inputted set of coordinates, the inputted predetermined angle of incidence and the inputted predetermined angle of approach;

moving the motors of the gimbal to set the circuit board to the inputted predetermined angle of incidence and the inputted predetermined angle of approach;

moving the motors of the Z-axis slide and the Y-axis actuator and the X-axis actuator of the gantry to set the circuit board to the calculated position; and displaying or capturing, from the set circuit board at the calculated position and at the predetermined angle of incidence and the predetermined angle of approach, an image of the point of interest for review, wherein the image can be inspected by at least one of a human inspector and an automated inspection system.

6. The method of claim 5 wherein calculating how to position the item results in a position to which the controller moves the X-axis actuator, a position to which the controller moves the Y-axis actuator, and a position to which the controller moves the gimbal by way of the respective motors thereof.

7. The method of claim 5 for inspecting a plurality of points of interest on the item, the item having a plurality of objects thereon, the method comprising:

accessing a first list having the plurality of objects of the item and for each object a position thereof on the item;

accessing a second list having the plurality of points of interest and for each point of interest an object of the first list on which the point of interest is located, a position on the object of the first list, and a desired angle of incidence and angle of approach for the captured image corresponding to the point of interest; and for each point of interest in the second list:

determining the object of the point of interest from the second list;

determining the position of the determined object on the item from the first list;

determining the position of the point of interest on the determined object from the second list;

determining the position of the point of interest within the system from the determined position of the determined object and the determined position of the point of interest on the determined object;

determining the desired angle of incidence and angle of approach for the displayed or captured image corresponding to the point of interest from the second list; and displaying or capturing an image of the point of interest based on the determined position of the point of interest within the system and the determined desired angle of incidence and angle of approach.

8. The method of claim 5 wherein the item is mounted to a first one of the Y-axis actuator and the X-axis actuator, the first one of the Y-axis actuator and the X-axis actuator is mounted to the second one of the Y-axis actuator and the X-axis actuator, and the second one of the Y-axis actuator and the X-axis actuator is mounted to the gimbal.

9. The method of claim 5 wherein the controller moves the item with respect to the imager while the imager is maintained as stationary.

10. The method of claim 5 wherein the gimbal holding the imager fixes the view of the imager to have a normalized orientation so that an 'up' direction in an image captured by the imager is always in a fixed direction with respect to the X-Y plane of the item.

11. The method of claim 5 further comprising defining the distance of the imager to the point of interest and comprising calculating how to position the imager to set the line of sight to the defined point of interest according to the received angle of incidence and angle of approach while maintaining the defined distance of the imager to the point of interest.

* * * * *